(12) United States Patent
Kaneko et al.

(10) Patent No.: US 6,221,354 B1
(45) Date of Patent: *Apr. 24, 2001

(54) IMMUNOLOGICAL TOLERANCE INDUCER KIT

(75) Inventors: Tetsuo Kaneko, Saitama; Yuka Nozaki, Kodaira; Yukiko Ishiguro, Tokyo; Tamotsu Kuwata, Saitama, all of (JP)

(73) Assignee: Meiji Milk Products Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/387,903

(22) Filed: Sep. 1, 1999

Related U.S. Application Data

(62) Division of application No. 08/787,107, filed on Jan. 22, 1997, now Pat. No. 5,951,984.

(30) Foreign Application Priority Data

Jan. 22, 1996 (JP) ........................................................ 8-8223

(51) Int. Cl.⁷ ............................ A61K 39/00; A23D 9/00; A23C 21/06; A23C 21/08
(52) U.S. Cl. ........................ 424/184.1; 426/601; 426/656
(58) Field of Search .................................. 426/601, 656; 424/184.1

(56) References Cited

FOREIGN PATENT DOCUMENTS

| | | |
|---|---|---|
| 1329544 | 5/1994 | (CA) . |
| 0271079 | 6/1998 | (EP) . |
| 5-5000 | 1/1993 | (JP) . |
| 7101873 | 4/1995 | (JP) . |
| 9427634 | 12/1994 | (WO) . |

OTHER PUBLICATIONS

Aramaki et al., Immnolo. Lett., 40:21–25 (1994).
Warner et al., J. Allergy Clin. Immunol., 66:336–341 (1980).
Shenassa et al., J. Allergy Clin. Immunolo., 75:177 (1985).
Trentham et al., Science, 261:1727–1729 (1993).
Dakin et al., Am. J. Med. Sci., 98–101 (1829).
Wells et al., J. Infect. Dis., 8:66–124 (1991).
Hanson et al., J. Immunolo., 123:2337–2343 (1979).
Ishii et al., Int. Arch. Allergy Appln. Immunl., 94:288–290 (1991).
Korenblatt et al., J. Allergy, 41:226–235 (1968).
Husby et al., J. Immunolo., 152:4663–4670 (1994).

*Primary Examiner*—Geetha P. Bansal
(74) *Attorney, Agent, or Firm*—Sughrue, Mion, Zinn, Macpeak & Seas, PLLC

(57) ABSTRACT

A method for inducing immunological tolerance in mammals which comprises feeding an antigen to a mammal, wherein the mammal is not allowed to ingest a fat-soluble component or a fat-soluble component-containing substance simultaneous with ingestion of the antigen, and an immunological tolerance inducing food kit and an immunological tolerance inducer kit which comprise an antigen-containing preparation containing no fat-soluble component and an antigen-free preparation containing no fat-soluble component. According to this invention, immunological tolerance can be induced effectively.

2 Claims, 8 Drawing Sheets

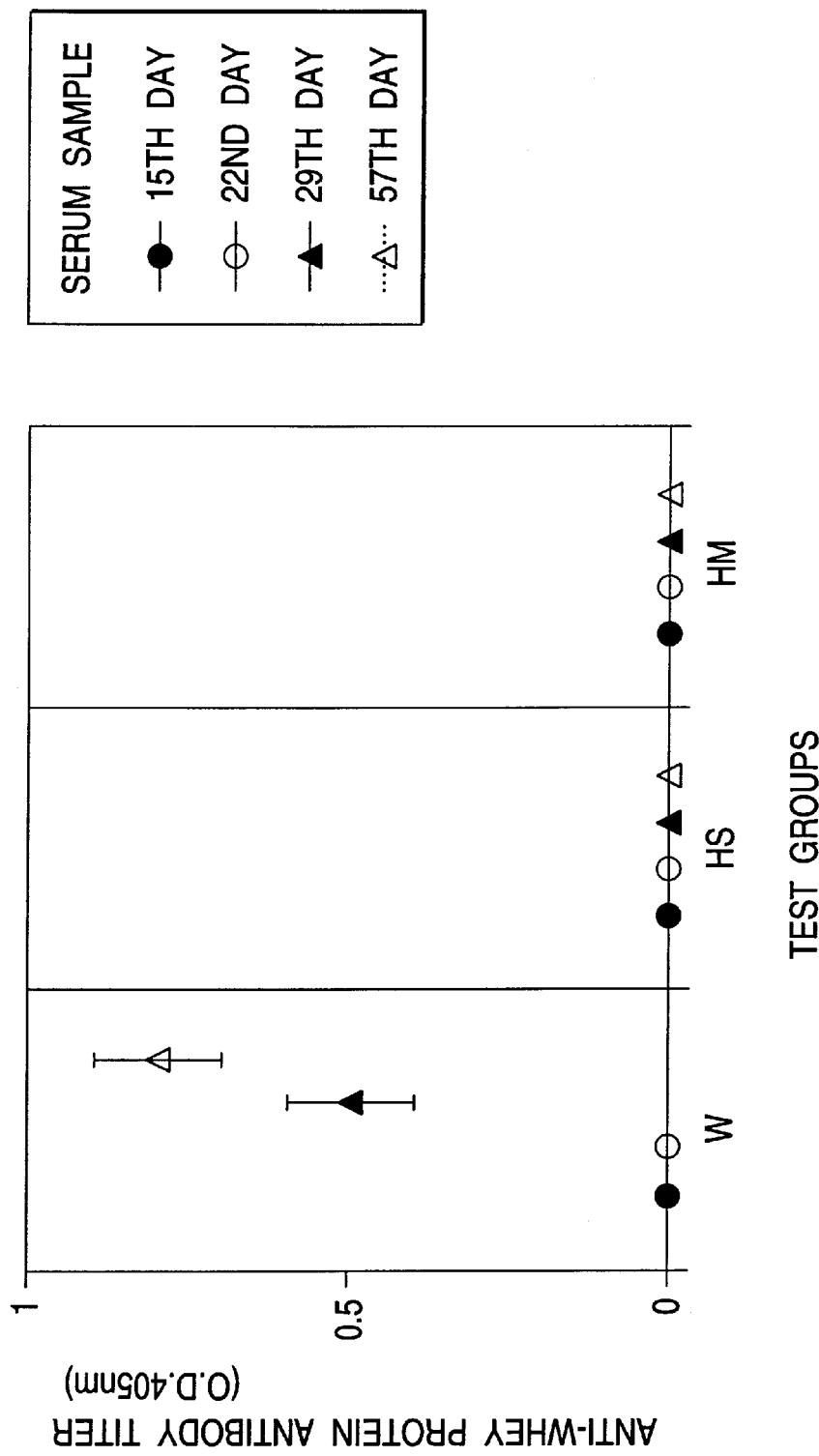

IMMUNOLOGICAL TOLERANCE INDUCER KIT

This is a divisional of application Ser. No. 08/787,107 filed Jan. 22, 1997 now U.S. Pat. No. 5,951,984, the disclosure of which is incorporated herein by reference.

FIELD OF THE INVENTION

The present invention relates to a method for preventing and treating crises of allergic reactions and immunological rejection reactions. Particularly, the present invention relates to a method for preventing and treating crises of allergic reactions, such as food allergy, pollen allergy, bee allergy, lacquer poisoning and the like, which are induced by ingestion or inhalation of antigens or percutaneous contact with antigens and immunological rejection reactions at the time of organ transplantation, which is effected based on the effective induction of immunological tolerance, and food and drugs using the method.

BACKGROUND OF THE INVENTION

A basic countermeasure to prevent recidivation of allergy is to avoid exposure to allergen. For example, in the case of food allergy, a countermeasure is taken by not eating allergen-containing food, refraining ingestion thereof or attenuating its allergenic property by thorough heating. In the case of pollen allergy, the most simple and effective countermeasure is to wear a mask or safety goggles or to refrain going out when drifting amount of pollen is large. These basic countermeasures are taken in daily life.

However, the object of these countermeasures is to prevent recidivation of allergic symptoms and not to perform fundamental treatment, although spontaneous remission may be expected in some cases.

In recent years, substitute milks for the mother's milk in which partially hydrolyzed peptide of milk protein is used as a nitrogen source have been put on the market to be used by familially allergic high risk babies for preventing crises of allergy. However, since there is no definite ground that the crises of milk allergy do not occur easily after changing to ordinary milk and dairy products, it is evident that these substitute milks are merely one of the choices to avoid antigens.

On the other hand, induction of the state of immunological tolerance is a therapeutic or preventive method in which its expected effects can be explained at least by its immunological mechanism. As examples of such a method, hyposensitization therapy and oral tolerance are known and have been carried out practically.

There are some reports in which percutaneous hyposensitization therapy is applied to treatments. Warner et al. disclose that a delayed asthmatic reaction induced by inhalant tick antigen was inhibited by hyposensitization therapy using a tick antigen preparation (Warner, J. O. et al., Lancet, 2:912 (1978)). Also, Norman et al. disclose that increase in the production of IgE antigen at a flowering time was inhibited by hyposensitization therapy using a urea-modified antigen IgE as a main antigen of ragweed pollen (Norman, P. S. et al., J. Allergy Clin. Immunol., 66:336 (1980)).

Patriarca et al. disclose oral hyposensitization therapy for treating food allergy (Patriarca, G. et al., eds., Food Allergy, Milano, Massom Italia, p.131 (1979)). Patriarca et al. have administered to patients who were allergic to milk, eggs or fruits, starting with a dose of 1 μg which was gradually increased thereafter by a factor of 1.5 for each step and finally succeeded in administering 10 g. Shenassa et al. disclose hyposensitization therapy of patients of peanut allergy (Shenassa, M. M. et al., J. Allergy Clin. Immunol., 75:177 (1985)). In the case of food allergy, however, the cause of the disease is an antigen which passed through the same route to begin with, and serious symptoms frequently occur even by an extremely small amount of the antigen, so that it seems to be difficult to carry out the treatment using a specific oral hyposensitization therapy without causing an allergic reaction because of a danger at least when un-treated antigen is used.

Recently, oral immunological tolerance is drawing attention as an effective method for treating autoimmune patients. Trentham et al. disclose the case of treating patients suffering from chronic rheumatoid arthritis (Trentham, D. E. et al., Science, 261:1727 (1993)). When each patient was allowed to ingest 0.1 to 0.5 mg of fowl II type collagen for 90 days in a total amount of 33 mg, the rheumatic symptoms were attenuated and 4 of 28 cases have completely recovered from the disease. Also, Weiner et al. disclose the clinical results of patients suffering from multiple sclerosis (Weiner, H. L. et al., Science, 259:1321 (1993)). A bovine myelin antigen containing myelin basic protein was administered to the patients with a dose of 300 mg a day for one year. Although significant effect was not found as a whole, an effect was observed in certain groups.

A living custom of Indians (Dakin, R., Am. J. Med. Sci., 4:98, (1829)) and lacquer artisans in relation to the prevention of lacquer poisoning is well known as a prior art means for inducing immunological tolerance for the purpose of prevention. They have learned from their ancestors that children who were forced to eat lacquer would hardly be poisoned with lacquer later, and this is still handed down by tradition.

Wells et al. have studied and reported the phenomenon of oral immunological tolerance for the first time as a science (Wells, H. G. et al., J. Infect. Dis., 8:66 (1991)). Wells et al. disclose that, when un-sensitized guinea pigs are allowed to ingest ovalbumin, an anaphylactic reaction cannot be induced using the antigen. In Hanson et al., an aqueous solution of ovalbumin was administered to mice of a highly ovalbumin-responding line by single and plural gastric administration and then the mice were immunized with the same antigen by intraperitoneal injection using aluminum hydroxide gel as the adjuvant (Hanson, D. G. et al., J. Immunol., 123:2337 (1979)). Hanson et al. disclose that, as a result, the production of serum anti-ovalbumin antibodies and reagin antibodies was inhibited almost completely.

Antigens which induce oral immunological tolerance are not limited to food antigens. Aramaki et al. disclose that, when an extract of ragweed pollen was orally administered to mice and then the same antigen was used in booster together with an adjuvant, production of specific IgE antibodies was inhibited (Aramaki, Y. et al., Immunol. Lett., 40:21 (1994)). Ishii et al. disclose that, when guinea pigs were immunized with a tick extract by parenteral administration using aluminum hydroxide as an adjuvant and then the extract was orally administered for 1 week, an oral hyposensitization effect was observed, because threshold value of a tick inhalation induction test and threshold value of histamine inhalation were increased, thereby discussing that oral hyposensitization therapy would be effective also upon pollen allergy (Ishii, A. et al., Int. Arch. Allergy Appl. Immunol., 94:288 (1991)).

It is said that aptness to cause induction of oral immunization is different depending on kinds of animals. According to reports so far published, it is considered that ruminants, rabbits and guinea pigs are resistant to the induction, and rodents such as mice, rats and the like are sensitive to the induction. Even in the case of human, a possibility of establishing oral immunological tolerance has been suggested by Korenblatt et al. and Lowney (Korenblatt, P. E. et al., J. Allergy, 41:226 (1968); Lowney, E. D., J. Invest. Dermatol., 512:411 (1968)). Recently, Husby et al. have asked a volunteer to ingest 0.5 g of hemocyanin of a shellfish, Macroschisma siensis, a protein which is not generally taken by human, and subcutaneous immunization was carried out thereafter, and suggested that immunological tolerance could be induced at least in T lymphocytes (Husby, S. et al., J. Immunol., 152:4663 (1994)).

In the above cases, all of the antigens are used in the form of aqueous solution as if a coincidence, but the reason for this is not described. Since comparison of these antigens with test groups in which other components are added is not described, it is evident that such an administration in the form of aqueous solution is not selected on purpose.

It is known in general that antigens having stronger property to induce immune response also have stronger property to induce immunological tolerance. Because of this, antigens to be used for the induction of the tolerance (tolerogens) are un-hydrolyzed in most cases. On the other hand, JP-A-5-5000 (the term "JP-A" as used herein means an "unexamined published Japanese patent application") and JP-A-7-101873 propose use of protein hydrolyzates for preventing crises of milk allergy. For example, in JP-A-5-5000, mice were provided with a solid feed preparation containing a peptide having a molecular weight of not more than 10,000 prepared by hydrolyzing casein or whey protein. Thereafter, each un-hydrolyzed sample of these proteins was intraperitoneally administered together with Freund's adjuvant to effect booster, thereby finding that production of specific antibodies was significantly low in comparison with the control group in which ion exchange water containing no peptide was provided. Since the antigenicity is reduced to a degree while maintaining the immunological tolerance function, it is concluded that these peptides having a molecular weight of not more than 10,000, namely partial protein hydrolyzates, are useful as food substances which can sufficiently activate the allergy defense mechanism.

However, the results in JP-A-5-5000 do not show that the tolerance induced by the pre-administration of the peptide prepared by partial protein hydrolysis is also effective in a case in which the original un-hydrolyzed protein is provided thereafter. The same can be said about the comparative group in which un-hydrolyzed protein was provided as the tolerance inducing antigen. To begin with, these results have a problem in that there is no comparative group in which the production of specific antibodies was said to be induced by continuous provision of un-hydrolyzed protein.

Although there are many reports on the use of percutaneous specific hyposensitization therapy as an effective symptomatic therapy of allergy (caused by food, pollen, ticks, house dust and the like), there is a danger of inducing shock and allergic symptoms such as asthma, fever and the like because of the injection of causal substances. Because of this, attempts have been made to inject these substances after attenuating their allergenic properties by polymerization, modification and the like, but complete avoidance of these actions have not been made.

Most serious problems of the percutaneous hyposensitization therapy are that the therapy requires a prolonged period of time which is at least several months and it gives pain in not a small degree. Accordingly, efforts for the treatment do not last long and are abandoned in the middle of the therapy in many cases. In addition, when it is prescribed as a therapy for children including babies, it causes emotionally difficult elements. Because of these factors, aside from the case in which it is used for the treatment of allergy, the percutaneous hyposensitization therapy is apt to be avoided when it is applied to the allergy prevention which has many uncertain elements, because its successive effects cannot be felt actually.

As a substitutive means for the percutaneous specific hyposensitization therapy having such problems, oral hyposensitization therapy is drawing attention in recent years. Since the oral hyposensitization therapy has an advantage of not causing pain of injection, it has been applied to the treatment of pollen and tick allergies, and its effects have also been recognized in a certain degree. In consequence, this therapy is expected to be useful for the fundamental prevention and treatment of various allergic diseases.

In the case of food allergy, however, the cause of disease is the ingested antigen in the first place, so that it is difficult to carry out the therapy using oral immunological tolerance without causing allergic reactions. Also, although there are many reports on animal experiments in which inhibitions of production of specific antibodies and delayed type reactions were observed and immunological tolerance was induced, the oral hyposensitization therapy still remains only as a possible candidate as a useful means to be applied to human because of the possible danger of establishing sensitization and inducing allergic symptoms.

The most important reason for the unstable effects of the oral hyposensitization therapy in the treatment of pollen and tick allergies and the hesitation in applying it to the prevention of the crises of food allergy is that nothing is known about a mechanism which decides selection of the completely incompatible phenomena of immunological tolerance and allergy induced by the ingested antigen.

SUMMARY OF THE INVENTION

In view of the above, an object of the present invention is to elucidate the mechanism of immunological tolerance induced by ingested antigens or inhibition thereof, thereby establishing a method which can induce immunological tolerance without causing allergic reactions based on the mechanism and providing food and drugs capable of inducing immunological tolerance.

Taking the above-described problems involved in the prior art into consideration, the inventors of the present invention have conducted intensive studies and found as the results that ingestion of a fat-soluble component greatly inhibits induction of immunological tolerance. Furthermore, unlike the case of reports so far published, re-exposure of antigens was evaluated in an actual mucous membrane-mediated pathway, namely ingestion, thereby confirming effective induction of immunological tolerance. Since these findings have rendered possible induction of specific antibodies by oral administration of antigens, which was difficult to effect in the prior art, a novel method for evaluating and confirming induction of immunological tolerance from a more practical angle was firstly established. By using this method, the present inventors have examined the above-described information further in detail and found as the results that it is essential to avoid ingestion of a fat-soluble component within a certain period after ingestion of antigens and to restrict ingestion of the component within a certain amount, in order to induce immunological tolerance. The present invention has been accomplished on the basis of these findings.

That is, this and other objects of the present invention have been attained by a method for inducing immunological tolerance in mammals which comprises feeding an antigen to a mammal, wherein the mammal is not allowed to ingest a fat-soluble component or a fat-soluble component-containing substance simultaneous with ingestion of the antigen.

Furthermore, this and other objects of the present invention have been attained by a method for inducing immunological tolerance in mammals which comprises feeding an antigen to a mammal, wherein the mammal is not allowed to ingest a fat-soluble component or a fat-soluble component-containing substance within 4 hours before and within 2 hours after ingestion of the antigen.

Moreover, this and other objects of the present invention have been attained by a method for inducing immunological tolerance in mammals which comprises feeding an antigen to a mammal, wherein the amount of a fat-soluble component or a fat-soluble component-containing substance ingested by the mammal within 4 hours before and within 2 hours after ingestion of the antigen is adjusted to an amount of not more than 0.1 g per kg weight of the mammal.

Still furthermore, this and other objects of the present invention have been attained by an immunological tolerance inducing food kit and an immunological tolerance inducer kit which comprise an antigen-containing preparation containing no fat-soluble component and an antigen-free preparation containing no fat-soluble component.

Still moreover, this and other objects of the present invention have been attained by an immunological tolerance inducing food kit and an immunological tolerance inducer kit which comprise an antigen-containing preparation containing no fat-soluble component and an antigen-free preparation containing a fat-soluble component, wherein the amount of the fat-soluble component ingested by a mammal within 4 hours before and within 2 hours after ingestion of the antigen-containing preparation is adjusted to an amount of not more than 0.1 g per kg weight of the mammal.

BRIEF DESCRIPTION OF THE DRAWINGS

FIG. 8 is a graph showing changes with the lapse of time in serum-specific antibody titer in mice fed with an enzyme hydrolyzate of whey protein as an immunological tolerogen.

DETAILED DESCRIPTION OF THE INVENTION

Figure 1:
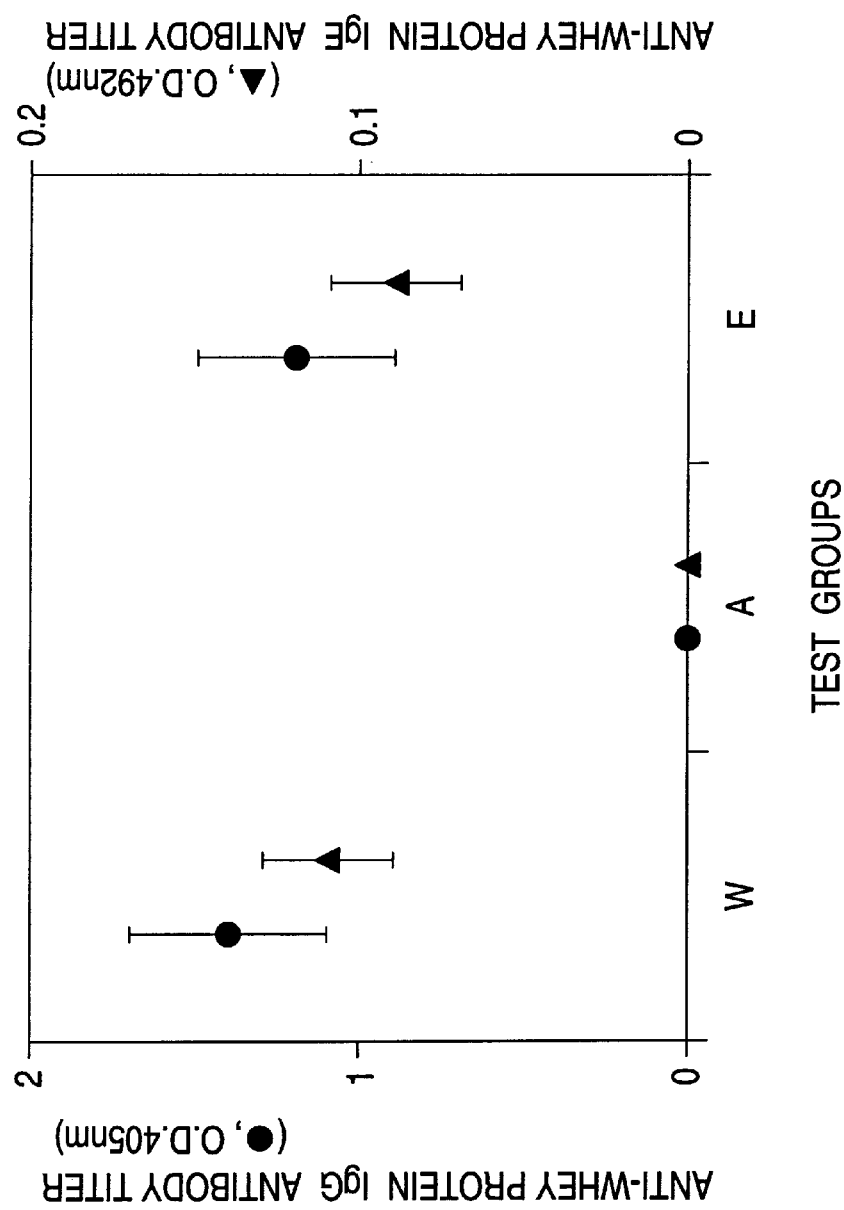
FIG. 1 is a graph showing results of ELISA (enzyme-linked immunosorbent assay) analysis of mouse serum anti-whey protein antibodies.

In the present invention, immunological tolerance can be induced by adjusting an ingestion amount of a fat-soluble component or a fat-soluble component-containing substance to a low level at the time of antigen ingestion by a mammal. Specifically, the ingestion amount of a fat-soluble component or a fat-soluble component containing-substance is adjusted to an amount of not more than 0.1 g, preferably not more than 0.05 g, per kg weight of a mammal, and more preferably, the mammal is not allowed to ingest a fat-soluble component or a fat-soluble component-containing substance.

Furthermore, preferably, immunological tolerance can be induced by adjusting the ingestion amount of a fat-soluble component or a fat-soluble component-containing substance to a low level within 4 hours, preferably 8 hours, before ingestion of antigens and within 2 hours, preferably 4 hours, after ingestion of antigens. Also in this case, the ingestion amount of a fat-soluble component or a fat-soluble component-containing substance within said period is adjusted to an amount of not more than 0.1 g, preferably not more than 0.05 g, per kg weight of a mammal, and more preferably, the mammal is not allowed to ingest a fat-soluble component or a fat-soluble component-containing substance.

The fat-soluble component for use in the present invention is one which is dissolved in an organic solvent, such as acetone, ether, chloroform-methanol mixture and the like, but is not dissolved in water, and includes various animal fats including fish oil, plant fats, phospholipids, fat-soluble vitamins and the like. These fat-soluble components are generally present in biological bodies and various natural substances as their constituting elements, and these components may be fractionated, concentrated or purified therefrom, or synthesized.

The term "antigen" as used herein means a general term for components which are recognized as "not self" and distinguished from "self" and substances which contain such components. Examples of familiar antigens include protein, peptide, food containing them as constituting elements, pollen and the like. Peptide may be a protein hydrolyzate or a synthesized product. Also, protein may be obtained by gene manipulation techniques.

Although it is convenient if fat-soluble components are removed from these antigens, it is not always necessary to purify them when the amount of fat-soluble components contained therein is reduced to such a level that the above-described conditions can be satisfied.

Since the method for inducing immunological tolerance of the present invention can be carried out by oral ingestion, it does not cause pain which is common in the case of percutaneous hyposensitization therapy and can be practiced easily. Such a method for inducing immunological tolerance is markedly useful in preventing and treating various allergic diseases such as food allergy, pollen allergy and the like and in attenuating rejection reactions at the time of the transplantation of organs and tissues. In this connection, the method of the present invention which relates to the induction of immunological tolerance is used in mammals including human.

Next, the immunological tolerance inducing food kit and immunological tolerance inducer kit of the present invention are described below.

The immunological tolerance inducing food kit of the present invention comprises an antigen-containing preparation containing no fat-soluble component and an antigen-free preparation containing a small amount of a fat-soluble component or no fat-soluble component. The antigen-containing preparation is not particularly limited as long as it contains an antigen and contains no fat-soluble component, and the antigen is not particularly limited, too.

Examples of the antigen-containing preparation include isolates of food proteins such as milk protein, the white of eggs, soybean protein and the like; protein extracts of pollen, ticks, house dust and the like; heat-modified products and partial hydrolysates thereof; synthetic peptide; and mixtures thereof. In addition, it may be a nutritious composition further enriched with appropriate saccharides, vitamins and electrolytes. These antigen-containing preparations are not necessarily in the form of isolated or purified products as long as the content of their fat-soluble components is reduced to such a level that it satisfies the conditions of the present invention. In consequence, it may be a skimmed milk prepared by repeating centrifugation to sufficiently remove milk fats, the white of eggs prepared by carefully avoiding contamination of the yolk or a mixture thereof.

The antigen-free preparation is not particularly limited as long as-it does not contain antigens and contains a small amount of a fat-soluble component or no fat-soluble component. Specific amount of the fat-soluble component is such that ingestion of the fat-soluble component becomes not more than 0.1 g, preferably not more than 0.05 g, per kg weight of a mammal within 4 hours, preferably within 8 hours, before ingestion of the antigen-containing preparation and within 2 hours, preferably 4 hours, after ingestion of the antigen-containing preparation.

Such an antigen-free preparation takes roles, at the time of the induction of immunological tolerance by ingesting the antigen-containing preparation, in avoiding influence of a fat-soluble component of the previously provided food and in supplementing nutrients and satisfying hunger. Examples thereof include drinking water, ordinary food or feed, an aqueous solution of amino acid mixture, a solution of water soluble vitamins, an electrolyte supplementing solution, a saccharide supplementing solution and the like, each which satisfies the above-described conditions.

In using the immunological tolerance inducing food kit, the antigen-free preparation is firstly used when a food substance containing a fat-soluble component is provided at least within 4 hours before its use. In the case of babies, their hunger can be satisfied by this. The antigen-containing preparation is then used at an optional time after 4 hours or more, preferably 8 hours or more, of the ingestion of a food substance containing a fat-soluble component. Ingestion of the preparation containing a fat-soluble component is avoided or the antigen-free preparation is used as a substitute, at least within 2 hours, preferably within 4 hours, after ingestion of the antigen-containing preparation.

After this treatment, ingestion of food containing a fat-soluble component can be made. In the case of babies, their nursing with mother's milk can be carried out. When mother's milk is not available, commercial milk preparations for allergic disease use may be used.

These treating steps are used as one cycle and carried out continuously or intermittently for a certain period. The amount of antigens to be fed and the required treating period cannot be specified indiscriminately because of individual differences, but the therapy is continued until establishment of immunological tolerance is fully confirmed by an immunological means. As a matter of course, exposure to the intended antigen must be avoided until immunological tolerance is induced.

Thus, immunological tolerance can be induced effectively by using the immunological tolerance inducing food kit of the present invention.

The immunological tolerance inducer kit of the present invention also comprises an antigen-containing preparation containing no fat-soluble component and an antigen-free preparation containing a small amount of a fat-soluble component or no fat-soluble component and can be fed orally. The antigen-containing preparation is not particularly limited as long as it contains an antigen containing no fat-soluble component, and the antigen is not particularly limited, too. As such a type of antigen-containing preparation, the same antigen-containing preparation of the above-described immunological tolerance inducing food kit can be used.

The antigen-free preparation is not particularly limited as long as it does not contain antigens and contains a small amount of a fat-soluble component or no fat-soluble component. Specific amount of the fat-soluble component is such that ingestion of the fat-soluble component becomes not more than 0.1 g, preferably not more than 0.05 g, per kg weight of a mammal within 4 hours, preferably within 8 hours, before ingestion of the antigen-containing preparation and within 2 hours, preferably 4 hours, after ingestion of the antigen-containing preparation.

Examples of the antigen-free preparation include an aqueous solution of amino acid mixture, a solution of water soluble vitamins, an electrolyte supplementing solution and a saccharide supplementing solution, various mixture solutions thereof and the like, each which satisfies the above-described conditions. Although not particularly limited, it may be used in the dosage form of solutions, powders, tablets, capsules and the like. Immunological tolerance can be induced effectively by using the immunological tolerance inducer kit in the same manner as the case of the above-described immunological tolerance inducing food kit.

Also, the immunological tolerance inducer kit of the present invention has no toxicity or extremely low.

Examples of the present invention are given below by way of illustration and not by way of limitation. Although milk protein is used as the antigen, and food oil and fat as the fat-soluble component, the antigen of the present invention is not limited to the milk protein, and the fat-soluble component is also not limited to the food oil and fat.

EXAMPLE 1

The following three preparations were prepared as sample solutions to feed mice (6-week-old female ddY mice, self-breeding after purchase from Japan SLC; the same shall apply hereinafter).

solution-w: ion exchange water solution-a: 2.5% aqueous solution of whey protein solution-e: emulsion containing 2.5% of whey protein and 1% of soybean oil Mice of three groups (groups W, A and E), each group consisting of 5 mice, were allowed to freely ingest the alphabetically corresponding sample solutions as drinking water for 14 days. During this period, each mouse drank 5 ml in average of each sample in one day. On the 15th day, each mouse was intraperitoneally immunized with 0.1 ml of an emulsion consisting of 1 volume of physiological saline containing 0.1% of whey protein and 1 volume of Freund's complete adjuvant. On the 29th day, immunization was carried out in the same manner using Freund's incomplete adjuvant. On the 36th day counting from the day of the commencement of sample solution ingestion, blood sample was collected from the tail vein to measure anti-whey protein IgE and IgG antibody titers in serum by ELISA (enzyme-linked immunosorbent assay).

Results of the measurement are shown in the graph of FIG. 1. When mice were immunized with whey protein by parenteral administration, the specific IgG and IgE antibody titers in group A provided in advance with the same protein in the form of aqueous solution were significantly lower than the antibody titers in group W provided with antigen-free ion exchange water. In group A, tolerance against the parenteral immunization was induced by the ingested whey protein.

On the other hand, the specific IgG and IgE antibody titers in group E provided in advance with whey protein together with the oil and fat were almost the same as those in group W provided with antigen-free ion exchange water and significantly high in comparison with those in group A. In group E, inhibition of immunological tolerance was observed.

It was shown that ingestion of the fat-soluble component inhibits induction of immunological tolerance by the oral antigen and maintains immune response against parenteral immunization carried out thereafter.

EXAMPLE 2

The following five preparations were prepared as sample solutions to feed mice.

solution-w: ion exchange water solution-a: 0.5% aqueous solution of whey protein solution-e: emulsion containing 0.5% of whey protein and 1% of soybean oil solution-ca: 0.5% aqueous solution of casein solution-ce: emulsion containing 0.5% of casein and 1% of soybean oil Mice of five groups (groups W, A, E, CA and CE), each group consisting of 5 mice, were allowed to freely ingest the alphabetically corresponding sample solutions as drinking water for 14 days. On the 8th, 15th, 22nd, 36th and 57th days counting from the day of the commencement of sample solution ingestion, blood samples were collected from the tail vein to measure anti-whey protein antibody titers and anti-casein antibody titers in sera by ELISA.

Figure 2:
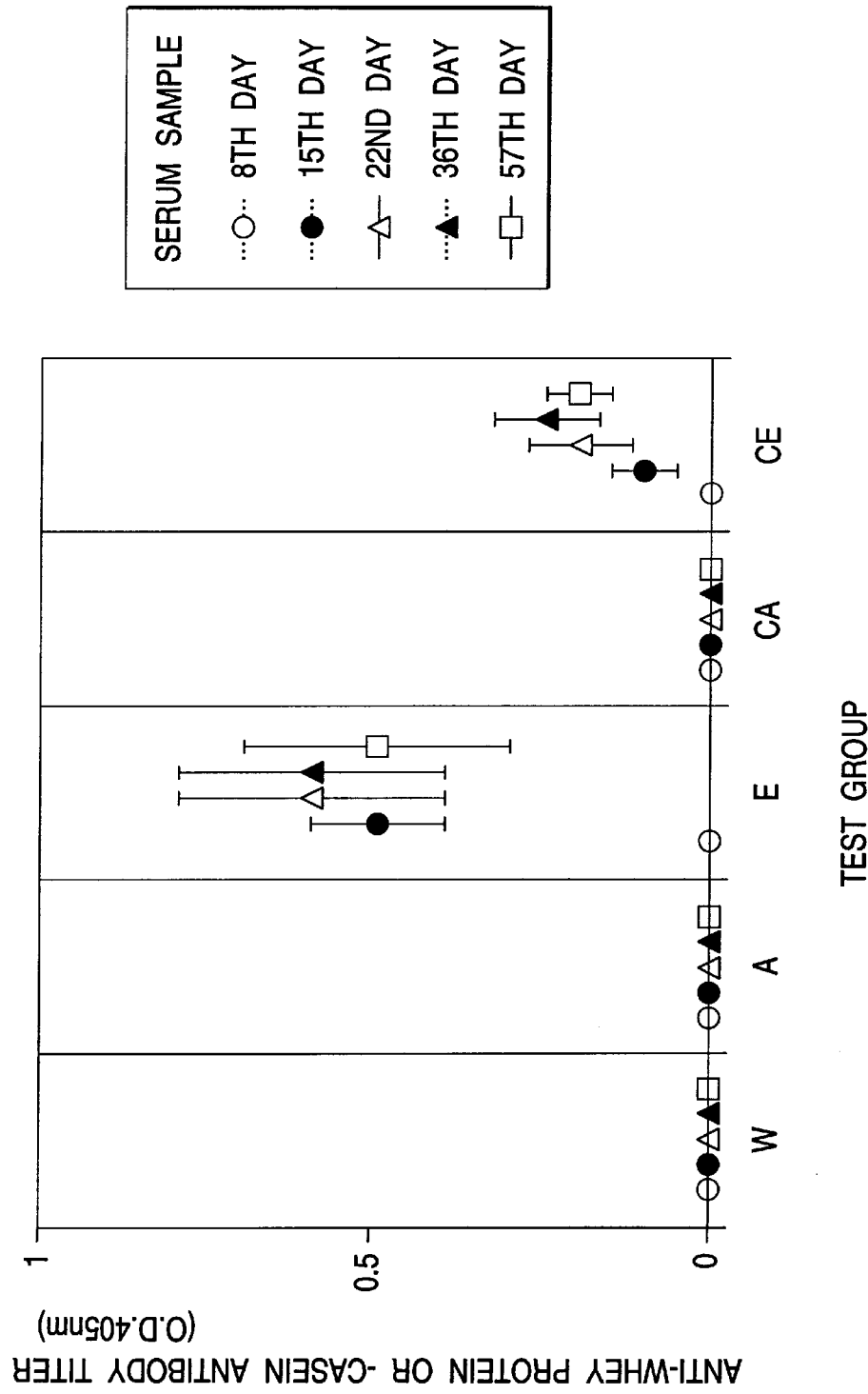
FIG. 2 is a graph showing changes with the lapse of time in serum-specific antibody titer in mice fed with milk protein containing or not containing soybean oil.

Results of the measurement are shown in the graph of FIG. 2. Similar to the case of the serum-specific antibodies in group W provided with antigen-free ion exchange water, the serum-specific antibodies in groups A and CA provided with protein in the form of aqueous solution were not detected until the 57th day. On the other hand, production of antibodies was clearly observed on and after the 15th day in groups E and CE provided with respective antigens together with the oil and fat in the form of emulsion.

Thus, it was shown that ingestion of the fat-soluble component inhibits induction of immunological tolerance by the oral antigens and maintains immune response against oral re-stimulation carried out thereafter. It was also shown that such an action of the fat-soluble component is exerted independent of the difference in the higher-order structure of these antigens.

EXAMPLE 3

The following four preparations were prepared as sample solutions to feed mice.

solution-w: ion exchange water solution-f: 12.5% aqueous solution of modified milk powder for nursing use (FK-P, manufactured by Meiji Milk Products Co., Ltd.)

solution-ha: 12.5% aqueous solution of whey protein trypsin hydrolysate having a molecular weight of not more than 10,000 solution-he: emulsion containing 12.5% of whey protein trypsin hydrolysate having a molecular weight of not more than 10,000 and 1% of soybean oil The trypsin hydrolysate used in solutions ha and he was prepared in the following manner.

A 50 kg portion of aqueous solution containing 5% by weight of separated whey protein (Davisco International Inc., USA) was prepared, heated to 45° C. and then adjusted to pH 8.0 with 3 N sodium hydroxide. This solution was mixed with swine trypsin (PTN 6.0S, Novo Nordisk, Denmark) in an amount of 1% by weight based on the substrate and stirred at pH 8.0 and 45° C. to carry out the enzyme reaction for 3 hours. After completion of the reaction, the reaction solution was adjusted to pH 7.0 with 3 N hydrochloric acid and subjected to flash heating at 120° C. for 15 seconds using a plate type heat exchanger, thereby inactivating the enzyme. The thus prepared enzyme hydrolysate was applied to a filtration apparatus equipped with an ultrafiltration membrane of 10,000 in molecular weight cutoff, and the resulting filtrate was freeze-dried to obtain a whey protein trypsin hydrolysate having a molecular weight of not more than 10,000.

Mice of three groups (groups W, HA and HE), each group consisting of 5 mice, were allowed to freely ingest solution-f as drinking water for 14 days. Starting on the 15th day, they were allowed to freely ingest the alphabetically corresponding sample solutions for 14 days. On the 8th, 15th, 22nd, 29th, 43rd and 64th days counting from the day of the commencement of solution-f ingestion, blood samples were collected from the tail vein to measure anti-whey protein antibody titers in sera by ELISA.

Figure 3:
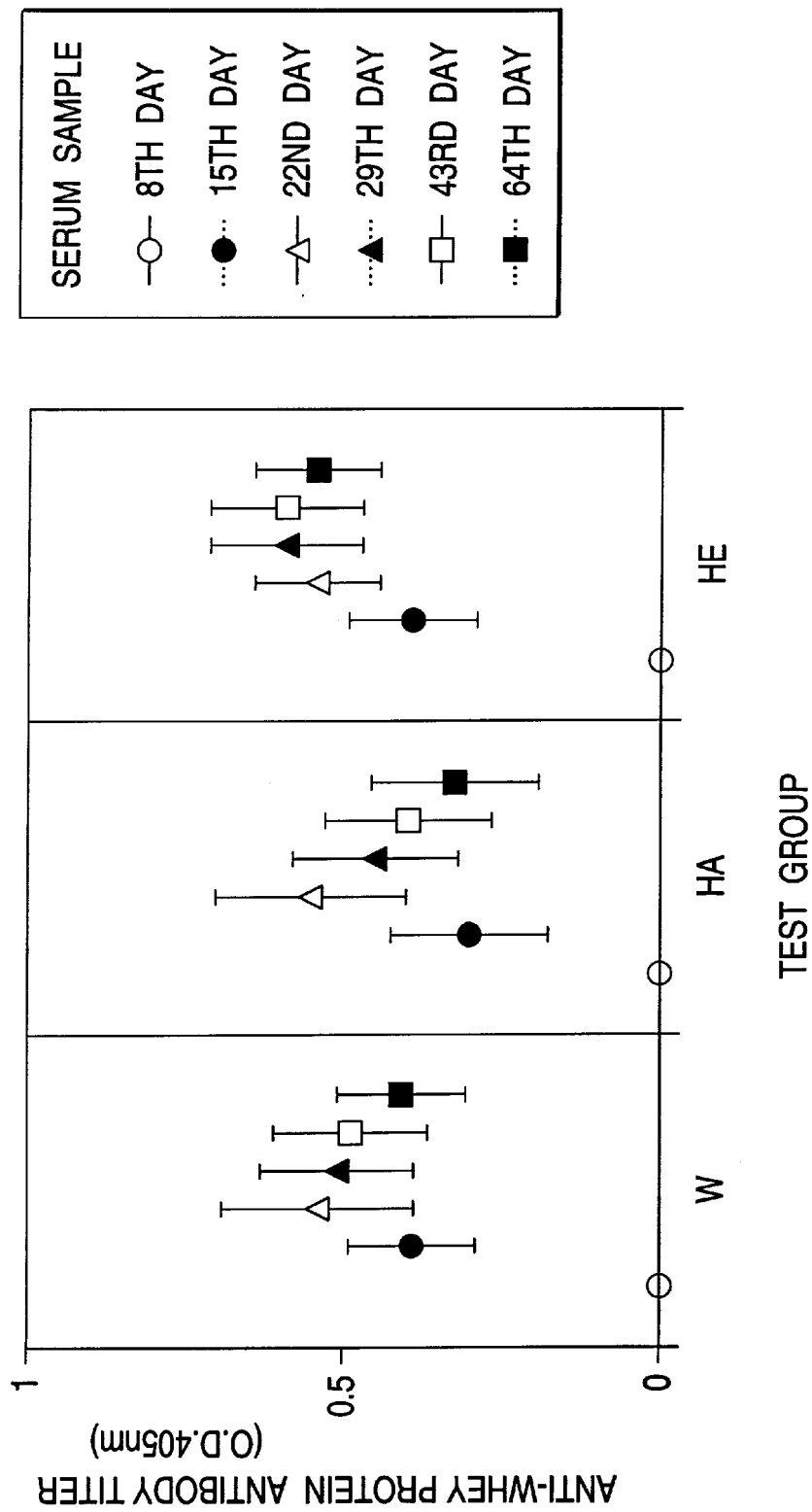
FIG. 3 is a graph showing changes with the lapse of time in anti-whey protein antibody titer in mice fed with a peptide solution after ingestion of modified milk powder.

Results of the measurement are shown in the graph of FIG. 3. In group HE provided with the trypsin hydrolysate together with the oil and fat, the specific antibody titer after termination-of the ingestion of modified milk powder solution decreased slightly on the 64th day. On the other hand, in group HA provided with the trypsin hydrolysate in the form of aqueous solution and in group W provided with antigen-free ion exchange water, decrease in the antibody titer was observed on the 29th day which was quicker than group HE. This tendency was more significant in group HA.

Thus, it was shown that, when induction of immunological tolerance is tried by the oral administration of peptide obtained by partial hydrolysis of the antigen under such conditions that the antigen sensitization is already established and production of antibodies can be found, ingestion of fat-soluble component strongly inhibits the immunological tolerance induction.

EXAMPLE 4

The sample solutions-a and -e of Example 1 were prepared.

solution-a: 2.5% aqueous solution of whey protein solution-e: emulsion containing 2.5% of whey protein and 1% of soybean oil Mice of two groups (groups A and E), each group consisting of 10 mice, were allowed to freely ingest the alphabetically corresponding sample solutions as drinking water for 7 days. Starting on the 8th day, a cross test of the ingestion antigen was carried out. That is, each group was divided into two sub-groups, each consisting of 5 mice, and one of the sub-groups was subjected to free ingestion of the same antigen solution used until the 7th day, and the other sub-group was subjected to free ingestion of the antigen solution given to thee other group, starting on the 8th day for 14 days (sub-groups Aa, Ae, Ea and Ee). On the 8th, 15th, 22nd, 29th, 43rd and 64th days counting from the day of the commencement of sample solution ingestion, blood samples were collected from the tail vein to measure anti-whey protein antibody titers in sera by ELISA.

Figure 4:
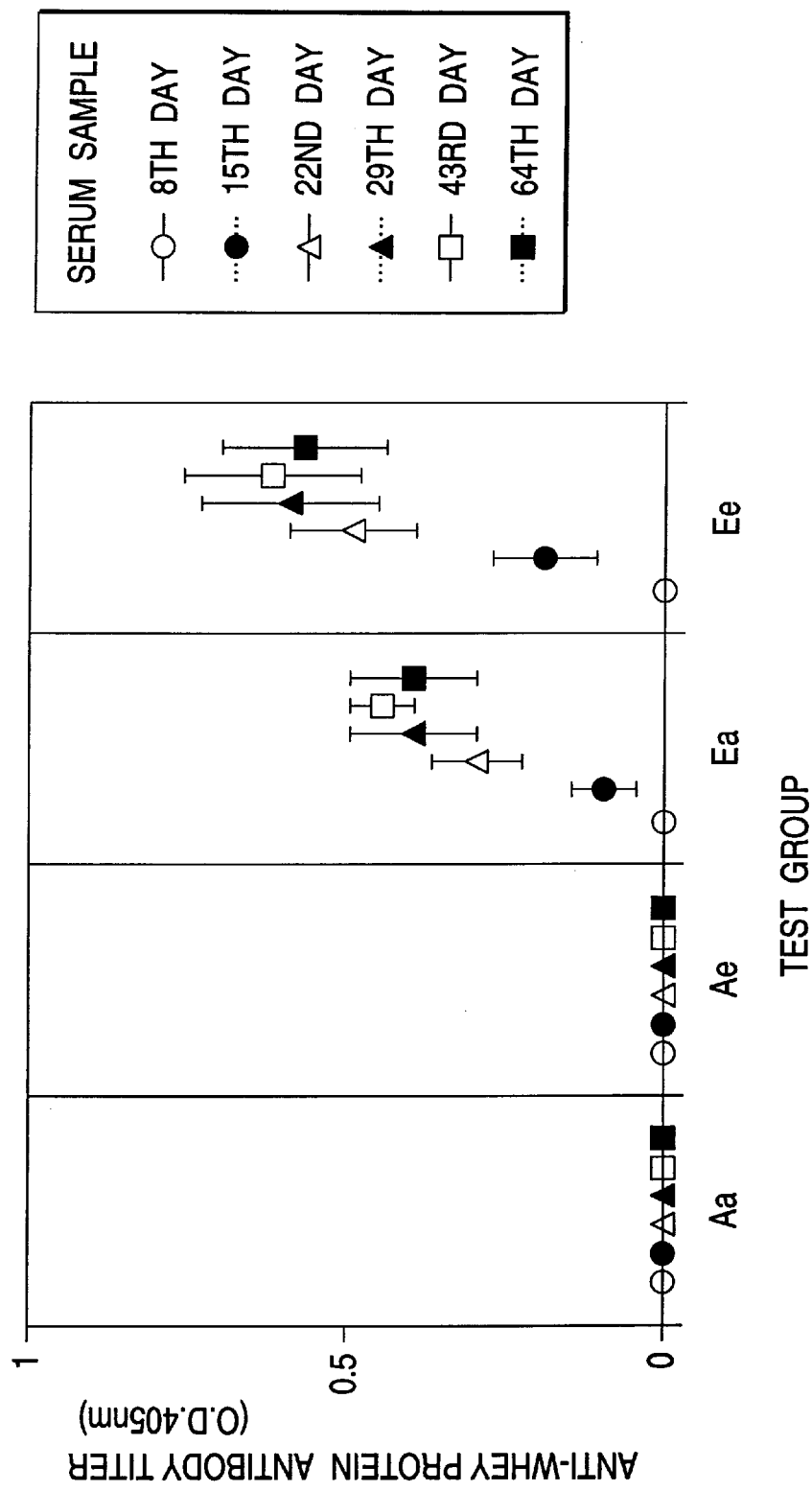
FIG. 4 is a graph showing changes with the lapse of time in serum anti-whey protein antibody titer in mice cross-fed with an aqueous solution and emulsion of whey protein.

Results of the measurement are shown in the graph of FIG. 4. In group A provided with the antigen in the form of aqueous solution for the initial 7 days, increase in the production of specific antibodies was not observed even in sub-group Ae subsequently provided with the antigen together with the oil and fat, similar to the case of sub-group Aa.

On the contrary, in group E provided with the antigen together with the oil and fat for the initial 7 days, production of specific antibodies was observed starting on the 15th day even in sub-group Ea subsequently provided with the antigen aqueous solution containing no oil and fat, similar to the case of sub-group Ee.

Thus, it was revealed that the establishment of immunological tolerance is markedly inhibited when the oil and fat are present at the time of the initial sensitization with the antigen.

Based on the results so far obtained, it was considered that the ingestion-amount of the fat-soluble component should be adjusted to a certain level or less or an interval of certain period or more should be arranged between the ingestion of a fat-soluble component and that of antigens. This point was examined in the following.

EXAMPLE 5

A total of 8 sample solutions shown in Table 1 (e0, e1, e2, e3, e4, e5, e6 and e7) were prepared.

TABLE 1

Compositions of whey protein sample solutions having different oil and fat concentrations

| Sample solution | Whey protein concentration (% (w/v)) | Soybean oil concentration (% (w/v)) | Dose soybean oil (g/kg-weight) |
|---|---|---|---|
| e0 | 12.5 | 0 | 0 |
| e1 | 12.5 | 25.0 | 2.0 |
| e2 | 12.5 | 12.5 | 1.0 |
| e3 | 12.5 | 6.25 | 0.5 |
| e4 | 12.5 | 2.5 | 0.2 |
| e5 | 12.5 | 1.25 | 0.1 |
| e6 | 12.5 | 0.625 | 0.05 |
| e7 | 12.5 | 0.25 | 0.02 |

Using a stomach tube, each of sample solutions-e0 to -e7 was administered to mice of 8 groups (groups E0 to E7, respectively), each group consisting of 5 mice (25 g in average weight), in a dose-of 0.2 ml per mouse once a day for 7 days. Starting on the 8th day, all mice were allowed to have free ingestion of sample solution-e1 which contained the highest oil and fat content for additional 14 days. On the 8th, 15th, 22nd, 29th, 43rd and 64th days counting from the day of the commencement of the administration, blood samples were collected from the tail vein to measure anti-whey protein antibody titers in sera by ELISA.

Figure 5:
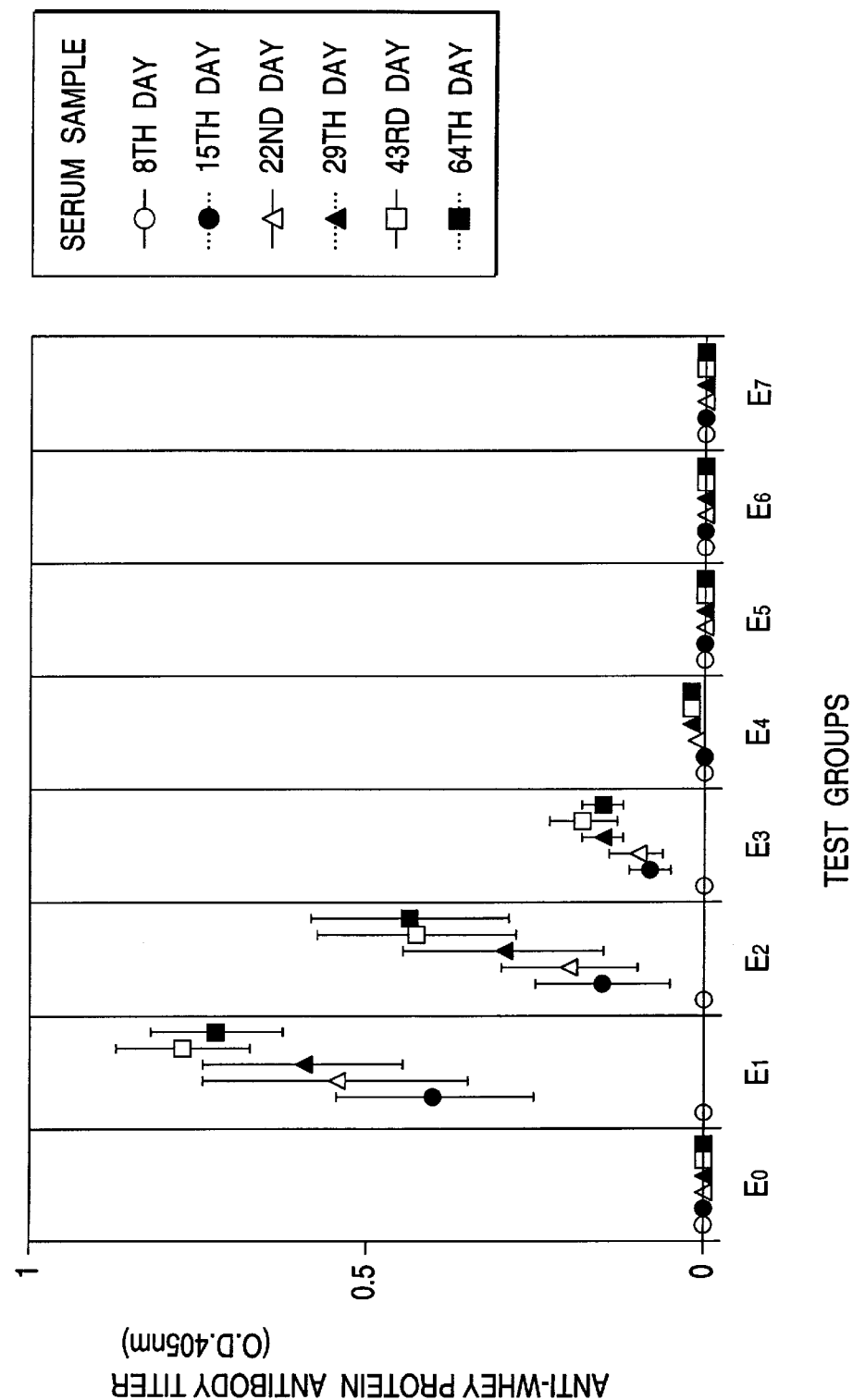
FIG. 5 is a graph showing changes with the lapse of time in serum anti-whey protein antibody titer in mice fed with different amounts of soybean oil at the time of initial administration of whey protein.

Results of the measurement are shown in the graph of FIG. 5. Production of antibodies was observed on the 15th day in groups E1 to E3 in which the amount of the oil and fat provided together with the antigen for the initial 7 days was 0.5 g or more per kg weight. The antibody titer was most significant in group E1. The antibody titers in groups E2 and E3 became obvious in all mice by the free ingestion of sample solution-e1 provided thereafter.

On the other hand, in groups E0 and E5 to E7 in which the amount of the oil and fat provided together with the antigen for the initial 7 days was not more than 0.1 g per kg weight, production of the specific antibodies was not found in all mice even after subsequent provision of sample solution-e1.

Thus, it was shown that the degree of antibody production against the ingested antigen strongly depends on the amount of the oil and fat ingested during the initial sensitization period. It was also shown that immunological tolerance works predominantly when the amount of the oil and fat is equal to or lower than a certain level, and the condition of immunological tolerance is maintained even if a large amount of the oil and fat are ingested thereafter simultaneously with the antigen.

More specifically, it was shown that induction of immunological tolerance can be made effectively by adjusting the amount of the fat-soluble component to be ingested during the initial sensitization period at a certain level or less, namely not more than 0.1 g, preferably not more than 0.05 g, per kg weight, even when the fat-soluble component is ingested thereafter simultaneously with the antigen.

EXAMPLE 6

The following sample solutions were prepared.

solution-a: 25% aqueous solution of whey protein solution-o: emulsion containing 25% ovalbumin and 50% soybean oil solution-e: emulsion containing 2.5% whey protein and 1% soybean oil Using a stomach tube, 0.1 ml of solution-a was administered into the stomach of each mouse of 9 groups, each group consisting of 5 mice, for 7 days. In this case, 0.1 ml of solution-o was administered into the stomach at a time corresponding to −8, −4, −2, −1, −0.5, 0, +1, +2 or +4 hours counting from the time of the administration of solution-a (group −8H to group +4H). In order to avoid ingestion of a fat-soluble component originated from solid food, mice were subjected to fasting during the period of from −8 hours to +4 hours.

Starting on the 15th day, all mice were allowed to have free ingestion of sample solution-e for 14 days. During this period, they were allowed to have free ingestion of the solid food. On the 8th, 15th, 22nd, 29th, 43rd and 64th days counting from the day of the commencement of the administration, blood samples were collected from the tail vein to measure anti-whey protein antibody titers in sera by ELISA.

Figure 6:
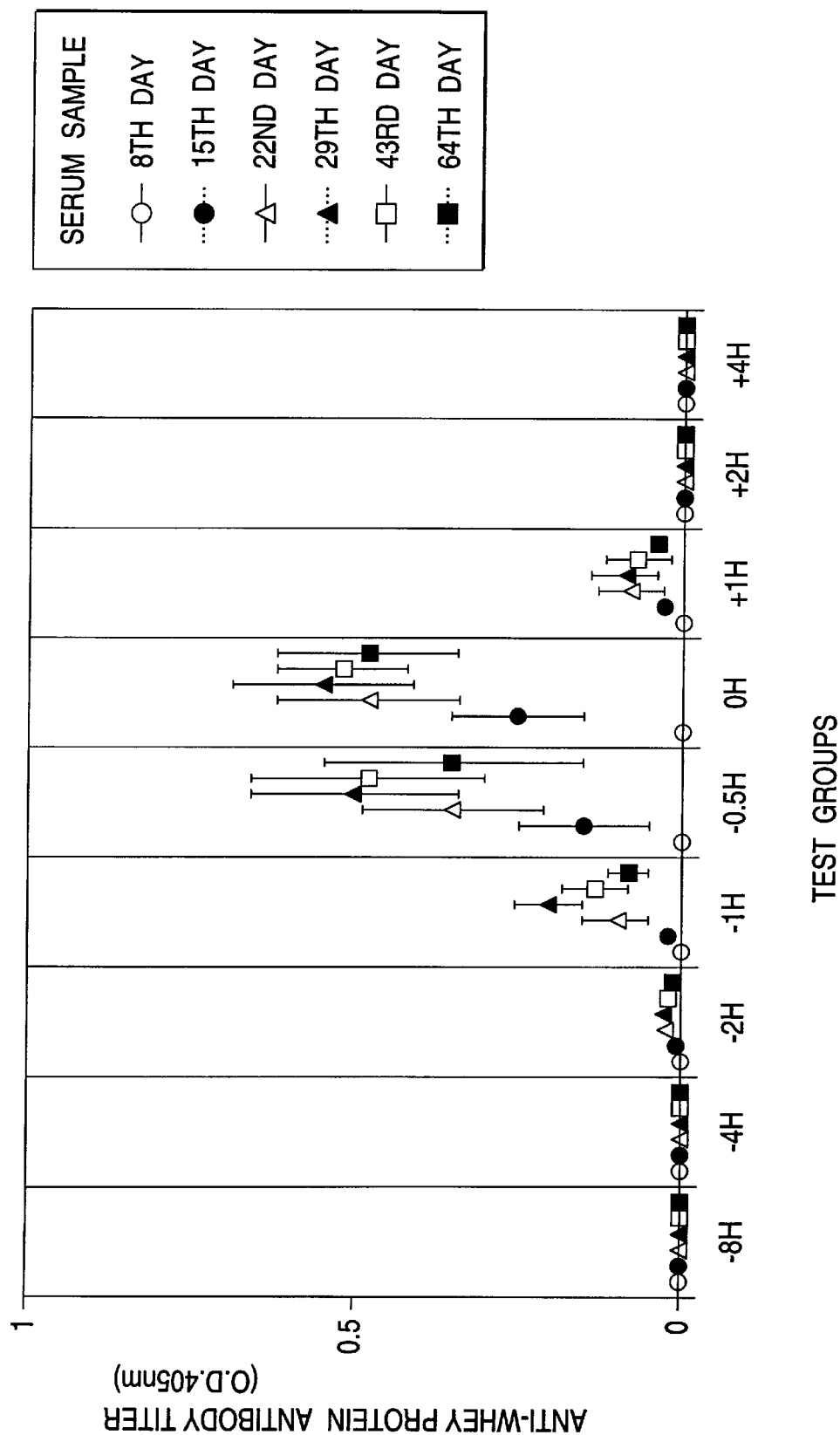
FIG. 6 is a graph showing changes with the lapse of time in serum anti-whey protein antibody titer in mice fed with a whey protein aqueous solution and soybean oil at different time interval.

Results of the measurement are shown in the graph of FIG. 6. Production of the specific antibodies increased as the interval between the administration of the whey protein antigen and the administration of the oil and fat was shortened. The highest accelerating effect was found in group 0H in which both components were administered at the same time, throughout the whole period. In groups −8H, −4H, +2H and +4H, on the other hand, production of the specific antibodies was not found throughout the whole period including the period after simultaneous administration of the oil and fat.

Thus, it was shown that the degree of antibody production against the ingested antigen strongly depends on the difference in the ingestion times of antigen and the oil and fat during the initial sensitization period. It was also shown that immunological tolerance works predominantly when a certain period or more of the interval is maintained, and the once established condition of immunological tolerance is maintained even if the oil and fat are provided thereafter simultaneously with the antigen.

More specifically, it was shown that induction of immunological tolerance can be made effectively by not allowing mice to ingest the fat-soluble component within a certain period of time during the initial sensitization period, counting from the time of antigen ingestion, namely within 4 hours before and 2 hours after the antigen ingestion, preferably within 8 hours before and 4 hours after the antigen ingestion.

EXAMPLE 7

The following four preparations were prepared as sample solutions to feed mice.

solution-w: deionized water solution-ha: aqueous solution containing trypsin hydrolysates of casein, whey protein, ovalbumin and soybean protein, having a molecular weight of not more than 10,000, each in a concentration of 3% solution-he: emulsion containing trypsin hydrolysates of casein, whey protein, ovalbumin and soybean protein, having a molecular weight of not more than 10,000, each in a concentration of 3%, and 2% of soybean oil solution-e: emulsion containing casein, whey protein, ovalbumin and soybean protein, each in a concentration of 0.5%, and 2% of soybean oil The aqueous solution used in solutions-ha and -he was prepared in the following manner.

A 10 kg portion of aqueous solution containing 5% of lactic casein (New Zealand Dairy Board, N.Z.), separated whey protein (Davisco International Inc., USA), ovalbumin (Wako Pure Chemical Industries, Ltd.) or soybean protein (Fuji Oil Company, Limited) was prepared, heated to 45° C. and then adjusted to pH 8.0 with 3 N sodium hydroxide. This solution was mixed with swine trypsin (PTN 6.0S, Novo Nordisk, Denmark) in an amount of 1% by weight based on the substrate and stirred at pH 8.0 and 45° C. to carry out the enzyme reaction for 3 hours. After completion of the reaction, the reaction solution was adjusted to pH 7.0 with 3 N hydrochloric acid and heated at 95° C. for 10 minutes, thereby inactivating the enzyme. The thus prepared enzyme hydrolysate was applied to a filtration apparatus equipped with an ultrafiltration membrane of 10,000 in molecular weight cutoff, and the resulting filtrate was freeze-dried. Thereafter, an aqueous solution containing the thus obtained trypsin hydrolysates having a molecular weight of not more than 10,000, each in a concentration of 3%, was prepared.

Using a stomach tube, each of the alphabetically corresponding sample solutions was administered to mice of three groups (groups W, HA and HE), each group consisting of 5 mice, in a dose of 0.2 ml per animal, once a day for 14 days. Starting on the 15th day, they were allowed to freely ingest solution-e instead of drinking water for 14 days. On the 15th, 22nd, 29th and 57th days counting from the day of the commencement of the administration, blood samples were collected from the tail vein to measure antibody titers in sera specific for respective proteins by ELISA.

Figure 7:
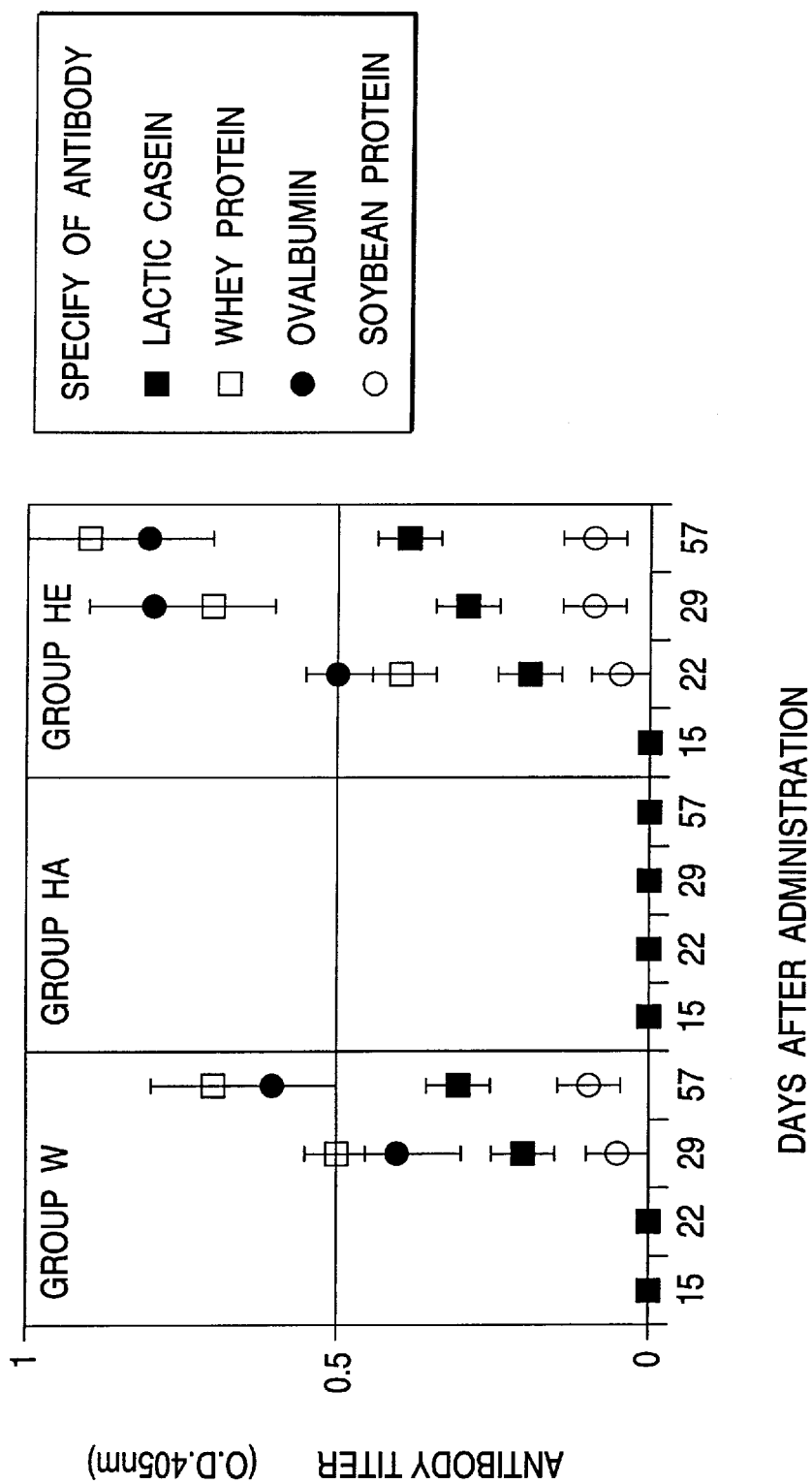
FIG. 7 is a graph showing changes with the lapse of time in serum-specific antibody titer in mice fed with an enzyme hydrolyzate of a mixture of proteins containing or not containing soybean oil, as an immunological tolerogen.

Results of the measurement are shown in the graph of FIG. 7. In group W in which deionized water was administered, production of antibodies was observed against all proteins on the 14th day after its change to solution-e. In group HE in which the trypsin hydrolysates were administered together with the oil and fat, the specific antibody titers increased slightly on the 15th day against all proteins, and rapidly increased on the 7th day after its change to solution-e. On the other hand, in group HA in which the trypsin hydrolysates were provided as an aqueous solution, the antibody titers were not detected against all proteins throughout the whole period until the 57th day.

Thus, it was shown that, when induction of immunological tolerance is attempted by oral administration of partially hydrolyzed antigen peptides, ingestion of a fat-soluble component strongly inhibits induction of the immunological tolerance independent of the type of antigens. It was shown on the contrary that, when ingestion of a fat-soluble component-is kept low, even a mixture of partially hydrolyzed peptides prepared from different antigens can induce the immunological tolerance effectively by its oral administration.

EXAMPLE 8

The following four preparations were prepared as sample solutions to feed mice.

solution-w: deionized water solution-hs: aqueous solution containing trypsin, chymotrypsin, papain and neutrase hydrolysates of whey protein, having a molecular weight of not more than 10,000, each in a concentration of 3% solution-hm: aqueous solution containing 12% of trypsin+chymotrypsin+papain+neutrase hydrolysate of whey protein, having a molecular weight of not more than 10,000 solution-e: emulsion containing 2% of whey protein and 2% of soybean oil

The whey protein hydrolysate used in solution-hs was prepared in the following manner.

A 10 kg portion of aqueous solution containing 5% of separated whey protein (Davisco International Inc., USA) was prepared for each of the enzymes trypsin (PTN 6.0S, Novo Nordisk, Denmark), chymotrypsin (800S, Novo Nordisk), papain (Papain W-40, Amano Pharmaceutical Co., Ltd., Nagoya) and neutrase (0.5L, Novo Nordisk), heated to 45° C. and then adjusted to pH 8.0 with 3 N sodium hydroxide.

This solution was mixed with each of the above-described enzymes in an amount of 1% by weight based on the substrate and stirred at pH 8.0 and 45° C. to carry out the enzyme reaction for 3 hours. After completion of the reaction, the reaction solution was adjusted to pH 7.0 with 3 N hydrochloric acid and heated at 95° C. for 10 minutes, thereby inactivating the enzyme. The thus prepared enzyme hydrolysate was applied to a filtration apparatus equipped with an ultrafiltration membrane of 10,000 in molecular weight cutoff, and the resulting filtrate was freeze-dried. Thereafter, an aqueous solution containing the thus obtained enzyme hydrolysates having a molecular weight of not more than 10,000, each in a concentration of 3%, was prepared.

On the other hand, the whey protein hydrolysate used in solution-hm was prepared in the following manner.

A 10 kg portion of aqueous solution containing 5% of separated whey protein (Davisco International Inc., USA), was prepared, heated to 45° C. and then adjusted to pH 8.0 with 3 N sodium hydroxide. This solution was mixed with each of trypsin (PTN 6.0S, Novo Nordisk, Denmark), chymotrypsin (800S, Novo Nordisk), papain (Papain W-40, Amano Pharmaceutical Co., Ltd., Nagoya) and neutrase (0.5L, Novo Nordisk) in an amount of 1% by weight based on the substrate and stirred at pH 8.0 and 45° C. to carry out the enzyme reaction for 3 hours. After completion of the reaction, the reaction solution was adjusted to pH 7.0 with 3 N hydrochloric acid and heated at 95° C. for 10 minutes, thereby inactivating the enzyme. The thus prepared enzyme hydrolysate was applied to a filtration apparatus equipped with an ultrafiltration membrane of 10,000 in molecular weight cutoff, and the resulting filtrate was freeze-dried. Thereafter, an aqueous solution containing the thus obtained enzyme hydrolysates having a molecular weight of not more than 10,000, in a total concentration of 12%, was prepared.

Using a stomach tube, each of the alphabetically corresponding sample solutions was administered to mice of three groups (groups W, HS and HM), each group consisting of 5 mice, in a dose of 0.2 ml per animal, once a day for 14 days. Starting on the 15th day, they were allowed to freely ingest solution-e instead of drinking water for 14 days. On the 15th, 22nd, 29th and 57th days counting from the day of the commencement of the administration, blood samples were collected from the tail vein to measure antibody titers in sera specific for respective proteins by ELISA.

Results of the measurement are shown in the graph of FIG. 8. In group W in which deionized water was administered, production of antibodies was observed on the 14th day after its change to solution-e. In group HM in which the hydrolysates obtained by the treatment with different enzymes were administered, production of antibodies was not observed throughout the whole period until the 57th day. Also, in group HS in which a mixture of these enzyme hydrolysates was administered, the specific antibody titers were not detected throughout the whole period until the 57th day.

Thus, it was shown that partially hydrolyzed peptides prepared by cross reaction using two or more enzymes simultaneously or continuously are effective in inducing immunological tolerance by oral administration. It was also shown that the use of a mixture of hydrolysates prepared by carrying out respective enzyme reactions separately, inactivating the enzymes and then mixing them is also effective depending on the properties of the enzymes.

EXAMPLE 9

As an example of the immunological tolerance inducing food kit, kit A and kit B shown in Table 2 were prepared. Kit A is an antigen-free composition containing no fat-soluble component, and kit B is a composition containing no fat-soluble component but contains the intended antigen for inducing immunological tolerance. Although compositions enriched with saccharides, minerals and vitamins are used in kits A and B, these nutrition-enriching components can be prepared as occasion demands. The dosage form of these kits is not particularly limited to powders or solutions and it may be tablets, capsules and the like depending on their use. In addition, the immunological tolerance inducing food kit can also be used as an-immunological tolerance inducer kit.

TABLE 2

Compositions of immunological tolerance inducing food kits A and B

| Components | | Kit A | | Kit B | |
| --- | --- | --- | --- | --- | --- |
| | | per 100 g dry weight | per 100 ml | per 100 g dry weight | per 100 ml |
| Tolerogen (N × 6.38) | g | 0 | 0 | 24.4 | 3.0 |
| Fat | g | 0 | 0 | 0 | 0 |
| Carbohydrate | g | 96.7 | 9.0 | 73.2 | 9.0 |
| (Lactose) | g | (43.0) | (4.0) | (32.5) | (4.0) |

TABLE 2-continued

Compositions of immunological tolerance inducing food kits A and B

| Components | | Kit A | | Kit B | |
| --- | --- | --- | --- | --- | --- |
| | | per 100 g dry weight | per 100 ml | per 100 g dry weight | per 100 ml |
| (Soluble polysaccharides) | g | (53.7) | (5.0) | (40.7) | (5.0) |
| Ash | g | 3.2 | 0.3 | 2.4 | 0.3 |
| Energy | kcal | 387 | 36 | 390 | 48 |
| Vitamin A | IU | 2580 | 240 | 1950 | 240 |
| Vitamin B1 | μg | 430 | 40 | 325 | 40 |
| Vitamin B2 | μg | 490 | 60 | 490 | 60 |
| Vitamin B6 | μg | 645 | 40 | 325 | 40 |
| Vitamin B12 | μg | 3.2 | 0.3 | 2.4 | 0.3 |
| Vitamin C | mg | 65 | 6 | 50 | 6 |
| Vitamin D | IU | 540 | 50 | 400 | 50 |
| Vitamin E | mg | 6.4 | 0.6 | 5 | 0.6 |
| Vitamin K | μg | 38 | 3.5 | 28 | 3.5 |
| Pantothenic acid | mg | 3.2 | 0.3 | 2.4 | 0.3 |
| Niacin | mg | 8.6 | 0.8 | 6.5 | 0.8 |
| Folic acid | μg | 100 | 10 | 80 | 10 |
| Inositol | mg | 38 | 3.5 | 28 | 3.5 |
| Taurine | mg | 43 | 4 | 32 | 4 |
| Calcium | mg | 540 | 50 | 400 | 50 |
| Magnesium | mg | 65 | 6 | 50 | 6 |
| Potassium | mg | 750 | 70 | 570 | 70 |
| Sodium | mg | 260 | 24 | 195 | 24 |
| Phosphorus | mg | 300 | 28 | 230 | 28 |
| Chloride | mg | 450 | 42 | 340 | 42 |
| Iron | mg | 750 | 0.7 | 6 | 0.7 |
| Copper | μg | 480 | 45 | 365 | 45 |
| Zinc | mg | 4.3 | 0.4 | 3.3 | 0.4 |
| Manganese | μg | 97 | 9 | 70 | 9 |

Kit B as an immunological tolerance inducing composition can be used alone, and it can also be used in combination with kit A when the ingestion of fat within 4 hours before and 2 hours after its administration, preferably within 8 hours before and 4 hours after its administration, cannot be adjusted to a level of not more than 0.1 g, preferably not more than 0.05 g, per kg weight.

Kit A is useful when it is necessary to induce oral immunological tolerance by administering kit B to babies nursed with mother's milk, with an artificial milk product for allergic disease use or with both of them. That is, when it is necessary to carry out lactation within 4 hours before and 2 hours after administration of kit B, and the milk to be provided is mother's milk or an artificial milk product for allergic disease use, both are rich in fat-soluble components, baby's hunger can be satisfied or nourishment can be supplemented by providing kit A instead of the milk, thereby rendering possible positive avoidance of the ingestion of fat within 4 hours before and 2 hours after administration of kit B, preferably within 8 hours before and 4 hours after its administration. In consequence, the use of kit A renders possible free lactation excluding the period for the immunological tolerance induction with kit B.

EXAMPLE 10

No toxicity was found when 1,000 mg/day of kit A and 1,000 mg/day of kit B, both prepared in Example 9, were orally administered by force to mice (6-week-old female ddY mice, self-breeding after purchase from Japan SLC).

Thus, as has been described in the foregoing, according to the present invention, immunological tolerance can be induced effectively.

While the invention has been described in detail and with reference to specific embodiments thereof, it will be apparent to one skilled in the art that various changes and modifications can be made therein without departing from the spirit and scope thereof.

This application is based on application No. Hei 8-8223 filed in Japan, the content of which is incorporated hereinto by reference.

What is claimed is:

1. An immunological tolerance inducing kit which comprises an antigen-containing preparation containing no fat-soluble component and an antigen-free preparation containing a fat-soluble component, wherein the antigen in the antigen-containing preparation is at least one immunogen selected from the group consisting of a protein and a peptide and wherein the amount of the fat-soluble component ingested by a mammal within 4 hours before and within 2 hours after ingestion of the antigen-containing preparation is adjusted to an amount of not more than 0.1 g per kg weight of the mammal.

2. An immunological tolerance inducer kit according to claim 1, wherein the at least one immunogen is selected from the group consisting of casein, whey protein, ovalbumin and soybean protein.

* * * * *